US00PP15703P3

(12) United States Plant Patent
Roose et al.

(10) Patent No.: US PP15,703 P3
(45) Date of Patent: Mar. 29, 2005

(54) MANDARIN HYBRID TREE NAMED 'TDE3'

(50) Latin Name: *Citrus reticulata*
Varietal Denomination: TDE3

(75) Inventors: Mikeal L. Roose, Riverside, CA (US); Timothy A. Williams, Riverside, CA (US); Robert K. Soost, Inverness, CA (US); James W. Cameron, Salem, OR (US)

(73) Assignee: The Regents of the University of California, Oakland, CA (US)

( * ) Notice: Subject to any disclaimer, the term of this patent is extended or adjusted under 35 U.S.C. 154(b) by 3 days.

(21) Appl. No.: 10/177,479

(22) Filed: Jun. 20, 2002

(65) Prior Publication Data

US 2003/0237121 P1 Dec. 25, 2003

(51) Int. Cl.[7] ..... A01H 5/00
(52) U.S. Cl. ..... Plt./202
(58) Field of Search ..... Plt./202, 201

*Primary Examiner*—Kent Bell
(74) *Attorney, Agent, or Firm*—Townsend and Townsend and Crew LLP

(57) ABSTRACT

A new mandarin hybrid called "TDE3" is distinguished by production of fruit that combine mid-season maturity, medium large fruit size, attractive deep orange rind color and virtual absence of seeds with rich fruit flavor.

9 Drawing Sheets

Genus and species: This application is directed to a description of TDE3, which is a mandarin orange tree (*Citrus reticulata*).

BACKGROUND OF THE INVENTION

The pedigree of TDE3 is shown in FIG. 1. In 1973, pollen from Encore (unpatented) mandarin was applied to stigmas of a tetraploid (Temple×4N Dancy) hybrid (unpatented) and the pollinated flowers were bagged to prevent insect pollination. Fruits were collected in winter 1974, seeds extracted from each fruit, and each seed was planted. The chromosome number of each seedling was determined and those identified as triploid seedlings were budded onto Troyer rootstock. The resulting trees were planted in the field in Riverside, Calif. in 1976. These trees were evaluated for tree vigor, bearing, and seediness, fruit favor, fruit color, and other fruit quality traits from bearing until 1985. Five trees were selected from the original population and repropagated by budding onto C-32 citrange, C-35 citrange, Troyer citrange, and trifoliate orange rootstocks. One of the five trees was chosen and called TDE3. Two trees of the selection now called TDE3 selection were planted in the field in Riverside in 1987. When they began fruiting (approximately in 1990), these trees were evaluated for the same tree and fruit quality traits as the original trees. In 1987, the selection now called TDE3 was chosen for additional testing because it combined medium or large fruit size, low seed number, rich fruit flavor, deep orange rind and flesh color, and acceptable peelability. Budwood of this selection was tested for viruses and other pathogens by the Citrus Clonal Protection Program and virus-free bud source trees were planted at Lindcove Research and Extension Center, Exeter, Calif. in 1991.

Using this virus-free budwood source, additional trees were propagated and planted at several California locations between 1993 and 1996. These included one location in the Coachella Valley (the Coachella Valley Agricultural Research Station—CVARS, 8 trees), Ojai (12 trees) and Santa Paula (4 trees) in Ventura Co., Valley Center (San Diego Co., 10 trees), and two locations in the San Joaquin Valley, (Lindcove Research and Extension Center, 8 trees and Orange Cove, 8 trees). These trial plantings provide most of the available data on TDE3. Several different rootstocks have been used in these evaluations, mostly Carrizo citrange, C35 citrange, Rich 16-6 trifoliate, Cleopatra mandarin, and Schaub rough lemon. The trees in Valley Center are topworked Valencia on Troyer citrange rootstock. In general, no major effects of these rootstocks on fruit quality of TDE3 were observed and no incompatibilities have been evident, but longevity of trees on various rootstocks is not known.

ASEXUAL REPRODUCTION

The plant known as TDE3 was first asexaully propagated in 1975 when buds were collected from hybrid seedling 73-46,47-1 and grafted onto Troyer citrange rootstock in a greenhouse at the University of California, Riverside, Calif., U.S.A. This tree was grown in a greenhouse and in 1976 it was planted in Field 6D, Row 12, Tree 2 at the Citrus Research Center, University of California, Riverside, Calif., U.S.A. Additional asexual propagation took place in 1986 when buds were collected from field tree 6D-12,2 and grafted onto 'C32' citrange and trifoliate orange rootstocks. These trees were planted in Field 6C, Row 29, Tree positions 19 and 20 respectively in 1987.

BRIEF SUMMARY OF THE INVENTION

The present invention provides a novel mandarin hybrid having the characteristics described and illustrated herein. The hybrid TDE3 produces fruit that combines mid-season maturity, medium large fruit size, attractive deep orange rind color and virtual absence of seeds with rich fruit flavor.

BRIEF DESCRIPTION OF THE DRAWINGS

FIG. 2 illustrates, clockwise from top left; a nine-year old tree of TDE3 on Carrizo rootstock; fruit on tree; branching pattern; flower buds; flowers; leaves; and shoots.

FIG. 3 illustrates fruit of TDE3 sampled from nine-year-old tree on Carrizo rootstock.

FIG. 4 illustrates the solids:acid ratio of TDE3 at Santa Paula, Calif. over five years. Points plotted are means of all samples collected on a given date. Solid lines connect means for sampling dates within the same season. The dashed line is a lineR regression of solids:acid on sampling date using data from all years. The regression equation and $r^2$ value are shown in each figure.

FIG. 5 illustrate the solids:acid ratio of TDE3 at Coacella Valley, Calif., CVARS, over five years. Points plotted are means of all samples collected on a given date. Solid lines connect means for sampling dates within the same Season. The dashed line is a liner regression of solids:acid on sampling date using data from all years. The regression equation and $r^2$ value are shown in each figure.

FIG. 6 illustrate the solids:acid ratio of TDE3 at Lindcove, Calif. over five years. Points plotted are means of all samples collected on a given date. Solid lines connect means for sampling dates within the same season. The dashed line is a liner regression of solids:acid on sampling date using data from all years. The regression equation and $r^2$ value are shown in each figure.

FIG. 7 illustrate the solids:acid ratio of TDE3 at Valley Center, Calif. over five years. Points plotted are means of all samples collected on a given date. Solid lines connect means for sampling dates within the same season. The dashed line is a liner regression of solids:acid on sampling date using data from all years. The regression equation and $r^2$ value are shown in each figure.

FIG. 8 illustrates the solids:acid ratio of TDE3 at Orange Cove, Calif. over five years. Points plotted are means of all samples collected on a given date. Solid lines connect means for sampling dates within the same season. The dashed line is a liner regression of solids:acid on sampling date using data from all years. The regression equation and $r^2$ value are shown in each figure.

FIG. 9 illustrate the solids:acid ratio of TDE3 at Ojai, Calif. over five years. Points plotted are means of all samples collected on a given date. Solid lines connect means for sampling dates within the same season. The dashed line is a liner regression of solids:acid on sampling date using data from all years. The regression equation and $r^2$ value are shown in each figure.

DETAILED DESCRIPTION OF THE INVENTION

Figure 1:
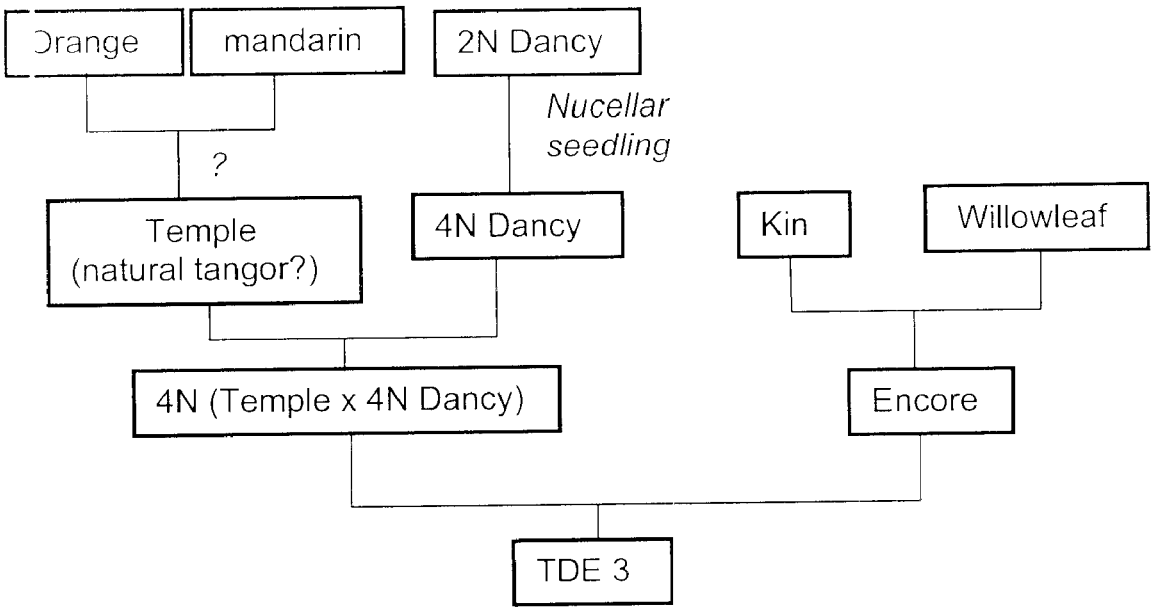
FIG. 1 illustrates the pedigree of TDE3. All cultivars are *C. reticulata* except orange, which is *C. sinensis*.

All major color code designations are by reference to The R.H.S. Colour Chart (2001) provided by The Royal Horticultural Society of Great Britain.

Eight to ten year-old trees grown in the ground were examined to prepare the description in this and the following paragraph. Tree shape (see FIG. 2) is approximately sphereoid, rather similar to that of orange trees. The trees have not been noted as particularly susceptible to any diseases and, based on a freeze in 1999, appeared only slightly more cold hardy than oranges of similar age. Leaves are simple, brevipetiolate, lanceolate, with entire or slightly sinuate margins (FIG. 2). The petiole shape is narrow and linear in shape. In comparison with most old-line citrus cultivars, trees of TDE3 are fairly thorny, with normal branches having short length (6 mm) thorns at about 13% of the nodes, and vigorous sprouts having long (27 mm) thorns at about 63% of nodes. Thorniness will probably decrease as the cultivar ages.

Flowers of TDE3 are typically hermaphroditic, with white (Green-White 157D, R.H.S. Colour Chart) petals and yellow (Yellow 13b, R.H.S. Colour Chart) anthers (FIG. 2). Trees flower from early April into May at most locations. Pollen is somewhat sparse, with 11% viability estimated in an in vitro germination test. Pollen tube growth is also less vigorous than that of other mandarins with high fertility. Many fruit are born inside the canopy, which limits sunburn.

The height and spread of a mature (27 years old) TDE3 tree is as follows: Tree height=5.5 m; Width=5.7 m. Trunk diameter of a 27 year old tree was 22.3 cm when measured 38 cm above the ground. Trunk color using The R.H.S. Colour Chart is Grey-Brown N199A. Trunk diameter increases for the life of the tree.

Leaf characteristics of TDE3 trees are as follows:

*Leaf shape.*—Ovate.
*Blade length.*—91.4 mm.
*Blade width.*—43.6 mm.
*Apex description.*—Acute with weak emargination.
*Base description.*—Convex.
*Abaxial color* (*R.H.S. chart*).—Yellow Green 146A.
*Adaxial color* (*R.H.S. chart*).—Yellow Green 147A.

Petiole characteristics of TDE3 trees are as follows:

*Petiole length.*—13.0 mm.
*Petiole width.*—2.0 mm.
*Petiole color* (*R.H.S. chart*).—Yellow Green 147A.

If sufficient fruit was available, 10-fruit samples were collected from each location two or three times each year beginning in 1997 or 1998. Generally samples were collected from two or three trees on each sampling date. These fruit were evaluated in Riverside for a range of traits as summarized in Table 1.

TABLE 1

Fruit characteristics of TDE3 averaged over 6 locations and 4 seasons. Samples were collected from November to April or May. "N" indicates the total number of fruit samples analyzed. Data are average over trees on various rootstocks. The trees examined for Table 1 ranged from 3–8 years old and were grown in the ground.

| Trait | N | Min | Max | Mean | SD |
|---|---|---|---|---|---|
| Fruit height (mm) | 286 | 42.0 | 80.4 | 56.2 | 6.96 |
| Fruit width (mm) | 287 | 50.0 | 99.7 | 66.0 | 8.07 |
| Fruit height:width | 286 | 0.64 | 1.00 | 0.85 | 0.054 |
| Rind color[a] | 287 | 4.0 | 13.0 | 11.9 | 2.22 |
| Rind texture[b] | 287 | 2.8 | 6.5 | 3.7 | 0.63 |
| Neck[c] | 287 | 0 | 2.50 | 0.79 | 0.673 |
| Peelability[d] | 287 | 5.00 | 10.00 | 8.20 | 0.953 |
| Rind thickness (mm) | 287 | 2.50 | 6.00 | 3.86 | 0.725 |
| Seeds per fruit | 287 | 0 | 5.00 | 0.29 | 0.580 |
| Fruit weight (g) | 283 | 71.5 | 290.5 | 134.4 | 42.93 |
| Juice content (%) | 279 | 22.5 | 72.2 | 47.5 | 7.21 |
| Soluble solids (%) | 279 | 5.50 | 16.90 | 11.99 | 2.184 |
| Acid (%) | 279 | 0.39 | 3.40 | 1.27 | 0.543 |
| Solids:acid | 279 | 3.60 | 26.52 | 10.78 | 3.916 |

[a]Visual rating on a scale of 0–13; 0 = green, 13 = red-orange
[b]Visual rating on a scale of 1–8; 1 = very smooth, 8 = extremely coarse
[c]Visual rating on a scale of 0–3; 0 = no trace of neck, 3 = neck with a diameter at least 50% of fruit diameter
[d]Subjective rating of ease of peeling a single fruit; 1 = very difficult, 10 = a fruit with completely separated rind and segments. Fruit with ratings of 7 or higher would be relatively easy to peel.

Based on this data, TDE3 fruit are oblate in shape (FIG. 3). The fruit base (stalk end) is convex, with some fruit having a small neck, and the apex (stylar end) is depressed (FIG. 3). The stylar scar is typically small and closed. The average fruit size is medium-large for a mandarin (classed as Jumbo by California state standards). Rind color of mature fruit is Orange-Red N30C (R.H.S. chart). The rind texture is variable, depending on tree age and crop. For older trees with a moderate to heavy crop, rind texture is papillate, with fairly conspicuous oil glands (FIG. 3). The rind of fruit from trees with very light crops is often excessively rough or bumpy. The rind is of medium thickness and easy to peel when fruit are mature, but can be much more adherent early in the season. Adherence of rind to pulp is medium or moderate. The fruit flesh color using The R.H.S. chart is Orange-Red N30D. Flesh thickness is about 59 mm. Albedo color is Orange-White 159A. Albedo thickness is about 2.0 mm. The number of segments per fruit is 11–12. The fruit is typically very juicy.

Important determinants of maturity date for citrus fruit are the solids:acid ratio and juice content. Although the overall juice content was high (>40%) in most samples, juice content was negatively correlated with sampling date at all 6 locations, and significantly so at CVARS and Lindcove. Drying of fruit was particularly evident in samples collected after early March at most locations. At CVARS, juice content declined between November and December in all three years for which samples were analyzed. Solids:acids ratio (FIG. 4) was significantly correlated with sampling date at all locations except Valley Center, where the range of sampling dates weas somewhat narrower. Using these regressions, the estimated dates on which fruit reached an 8:1 solids:acid ratio was November 1 for CVARS, December 15 for Valley Center and Ojai, January 8 for Orange Cove, January 12 for Lindcove, and January 20 for Santa Paula.

Yield of TDE3 was evaluated from visual ratings of crop relative to tree size at each location from 1998–99 to 2001–2002. The rating scale ranged from 0 (no crop) to 5 (very heavy crop). The topworked trees in Valley Center showed the highest and most consistent crops, ranging between 2 and 4.5 over the 4 years studied. Crops at Ojai were also good, being 1.5 or greater in all years. At Lindcove, Orange Cove, and Santa Paula, crop ratings indicated alternate bearing, with values of about 3, 0.5, and 1.5–4 in the last 3 years. Yield at Lindcove in 2000 and 2001 was 53 and 4.6 kg tree$^{-1}$, while at Orange Cove it was 63 and 0 kg tree$^{-1}$.

Trees that were screened to exclude bees during flowering produced very few fruit for two consecutive years, but it is possible that TDE3 is self-fertile but requires pollination for fruit set.

As discussed above, tree fruit is set in April and May. First and last harvest dates for Riverside, Calif. are estimated as January 15 and March 30.

Two siblings of TDE3, "TDE2" and "TDE4," were compared to TDE3. TDE3 is distinct from these cultivars in having the earliest maturity date, a less oblate shape, and distinctive flavor. The rind color of TDE4 is usually deeper orange than that of TDE3. Trees of fruit of TDE3 can be distinguished from those of other mandarins, including TDE2 and TDE4, using simple sequence repeat (SSR) DNA markers. Using TDE3 DNA as template, PCR primer set CAC15 (F=TAAATCTCCACTCTGCAAAAGC, R=GATAGGAAGCGTCGTAGACCC) amplified a band of 158 bp, while TDE2 and TDE4 both had two bands of 149 and 158 bp. Bands amplified with TAA15 (F=GAAAGGGTTACTTGACCAGGC, R=CTTCCCAGCTGCACAAGC) combined with those amplified with CAC15, TAA33 (F=GGTACTGATAGTACTGCGGCG, R=GCTAATCGCTACGTCTTCGC) and TAA03 (F=AGAGAAGAAACATTTGCGGAGC, R=GAGATGGGACTTGGTTCATCACG) distinguished TDE3 from the following cultivars: Dancy (unpatented), Temple (unpatented), Encore (unpatented), King (unpatented), Willowleaf (unpatented), Wilking (unpatented), Gold Nugget (unpatented), Pixie (unpatented), W. Murcott Afourer (unpatented), Ellendale (unpatented), Hernandina Clementine (unpatented), Fortune (unpatented), Kara (unpatented), Kinnow (unpatented), Murcott (unpatented), Nova (unpatented), and Ponkan (unpatented).

This paragraph and the following paragraph provide a comparison of TDE3 and its parental cultivars, 4N (Temple× 4N Dancy) and 'Encore'. The seed (female) parent of TDE3 is a tetraploid hybrid between a 'Temple' tangor and a tetraploid tree of 'Dancy' mandarin. The tetraploid (Temple×4N Dancy) parent (referred to below as 4N-TD) was never released by the University of California and only two trees of this variety exist. TDE3 is distinct from this variety in having less than 1 seed per fruit while 4N-TD averages 10 seeds per fruit. Fruit of 4N-TD have an aspect ratio of about 0.88, mature in December–January and hold on the tree for about 1 month, while those of TDE3 have an aspect ratio of about 0.85, mature in late January and hold on the tree for 2 months. Fruit of 4N-TD have thicker rinds (5.5 mm) than those of TDE3. Trees of 4N-TD are somewhat smaller (3.8 m tall) than those of TDE3 (5.5 m tall).

The pollen (male) parent of TDE3 is 'Encore' mandarin. TDE3 differs from 'Encore' in that 'Encore' fruit average about 20 seeds per fruit while fruit of TDE3 have less than 1 seed per fruit. 'Encore' fruit mature in March–April, about 2 months later than those of TDE3. Encore fruit always have a distinctive green or dark brown spot or blotch on the rind which is absent on TDE3 fruit. The average size of TDE3 fruit is larger than that of Encore. Encore fruit have an aspect ratio of 0.71 and much thinner rinds (2.0 mm) while those of TDE3 have an aspect ratio of 0.85 and rinds 3.5 mm thick. Encore fruit hold extremely well on the tree (4–6 months). The height of mature (35 year old) 'Encore' trees is about 4.1 m, shorter than that of mature (27 year old) TDE3 trees.

During the 1999–2000 and 2000–01 seasons, fruit of TDE3 and various other mandarin varieties were harvested and evaluated by a taste panel. In some cases, evaluations were done before and after storage at two different temperatures. Fruit were rated on a 9 point scale, where a score of 1 is "Dislike extremely", 5 is "Neither dislike or like", and 9 is "Like extremely".

Vigor of TDE3 trees has varied greatly across locations. At CVARS, canopy volumes of 7-year-old trees averaged 21.1 m$^3$. In contrast, at the cooler Santa Paula and Ojai locations, 7-year-old trees averaged 6.2 and 3.6 m$^3$. 7-year-old trees at Lindcove and Orange Cove averaged 9.9 and 7.3 m$^3$. Trees at CVARS have had very small crops relative to tree size, perhaps contributing to greater vegetative growth. Size of the topworked trees in Valley Center has not been measured since they are not comparable to trees in other locations, but in general the topworked trees are quite vigorous. Trees on Schaub rough lemon were larger than those on Carrizo citrange or C35 citrange at Santa Paula and Ojai. At Lindcove and CVARS, trees on Rich 16-6 trifoliate and Cleopatra were smaller than those on Carrizo and C-35 citranges. Fruit from trees on Schaub rough lemon generally have slightly lower solids and acid than those from trees on Carrizo citrange, C35 citrange, or trifoliate orange, but this effect is less noticeable than with oranges. No evidence of stock-scion incompatibilities was evident.

The most comparable mandarin is W. Murcott Afourer, which generally has a smoother rind than TDE3. However, when pollinizers are present, TDE3 has fewer seeds than W. Murcott Afourer. For example, data from a mixed planting in Riverside shows fruit of W. Murcott Afourer average 7.2 seeds per fruit, while those of TDE3 average about 0.5.

Storage and Sensory Evaluation of TDE3 were performed. Fruit were sampled from test plots at Lindcove and Orange Cove, run over a packline at the University of California Lindcove Research and Extension Center and waxed on Jan. 21, 2000. The fruit were stored 11 days at 68° F., 12 days at 37° F. followed by 7 days at 55° F., or 12 days at 41° F. followed by 7 days at 55° F. These samples represent early-season fruit of TDE3, the fruit from Lindcove and Orange Cove having solids:acid ratios of 7.6 and 6.8, respectively. Their ratings were good for all traits before storage, and were slightly changed or improved by both cold storage treatments. Storage at 68° F. reduced scores for visual appeal and peelability.

Overall, in comparison with the other cultivars sampled, later season samples generally were liked for taste or peelability by the panels. Storage tests indicate that TDE3 fruit can be stored at cold temperatures for at least 12 days without greatly affecting visual appeal or taste.

TDE3 can be propagated on many available citrus rootstocks by budding. To reduce thorniness, budwood should be selected from thornless, upper canopy branches. Tree spacing in field plantings will depend on vigor of the rootstock. For Carrizo citrange rootstocks, a recommended tree density is about 150 trees per acre. Higher densities are possible, but will require more frequent pruning or hedging. Care of young trees should be similar to that used for other mandarins or oranges. Trees have performed best in locations with more moderate climates such as the inland valleys of southern California. Trees can be grown with pollinizer cultivars such as Minneola, Valencia orange, or unrelated mandarins (not Temple, Dancy, Encore or other TDE hybrids) that produce viable pollen. Optimal pruning practices have not yet been developed, but in many locations trees will perform well with relatively little pruning. Maturity dates will vary with location, probably depending on the number of heat units and soil conditions.

As in some other mandarins, sprays with gibberellic acid may increase fruit set when pollinizers and/or pollinators are inadequate.

Trees are winter hardy in USDA zones 9b to 11.

What is claimed is:

1. A new and distinct variety of mandarin hybrid tree having the characteristics described and illustrated herein.

* * * * *

Figure 2. TDE3
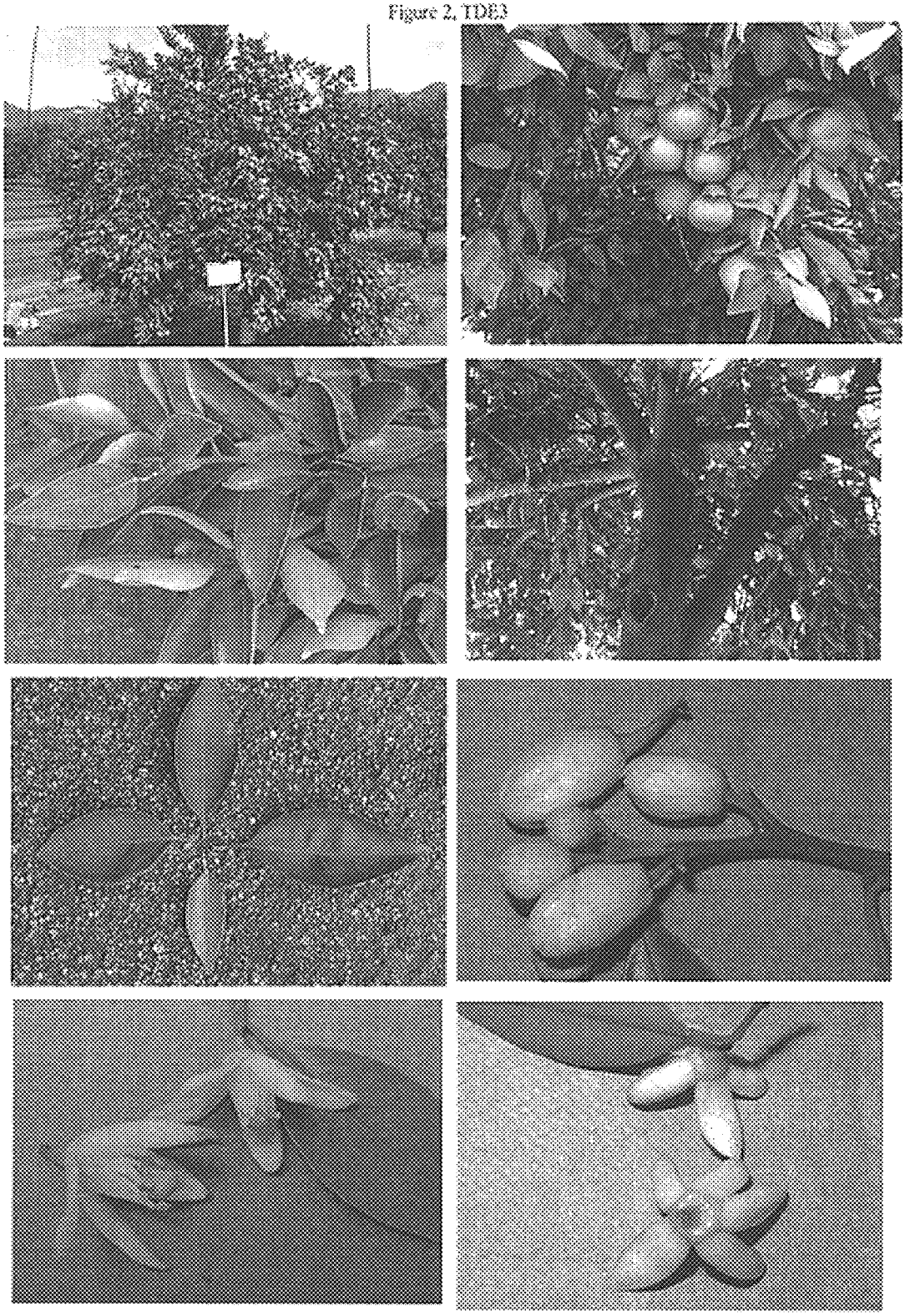

Figure 3, TDE3
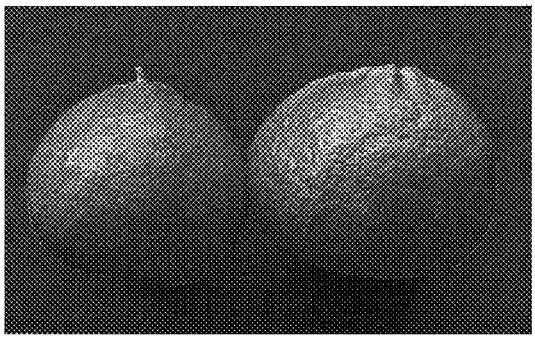
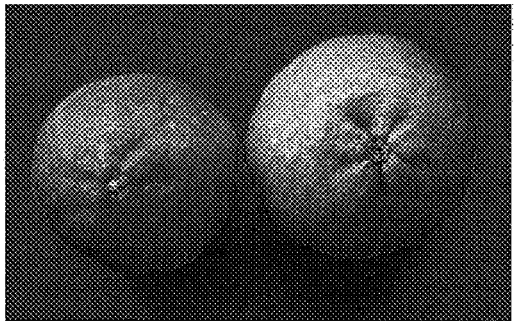
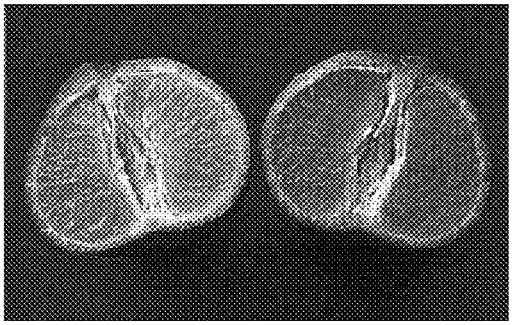
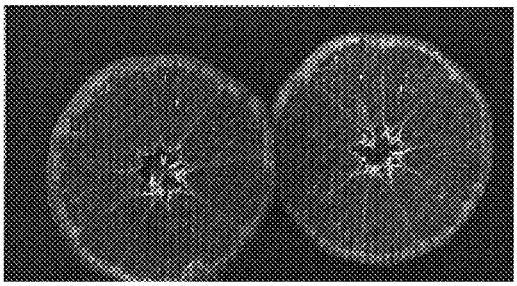

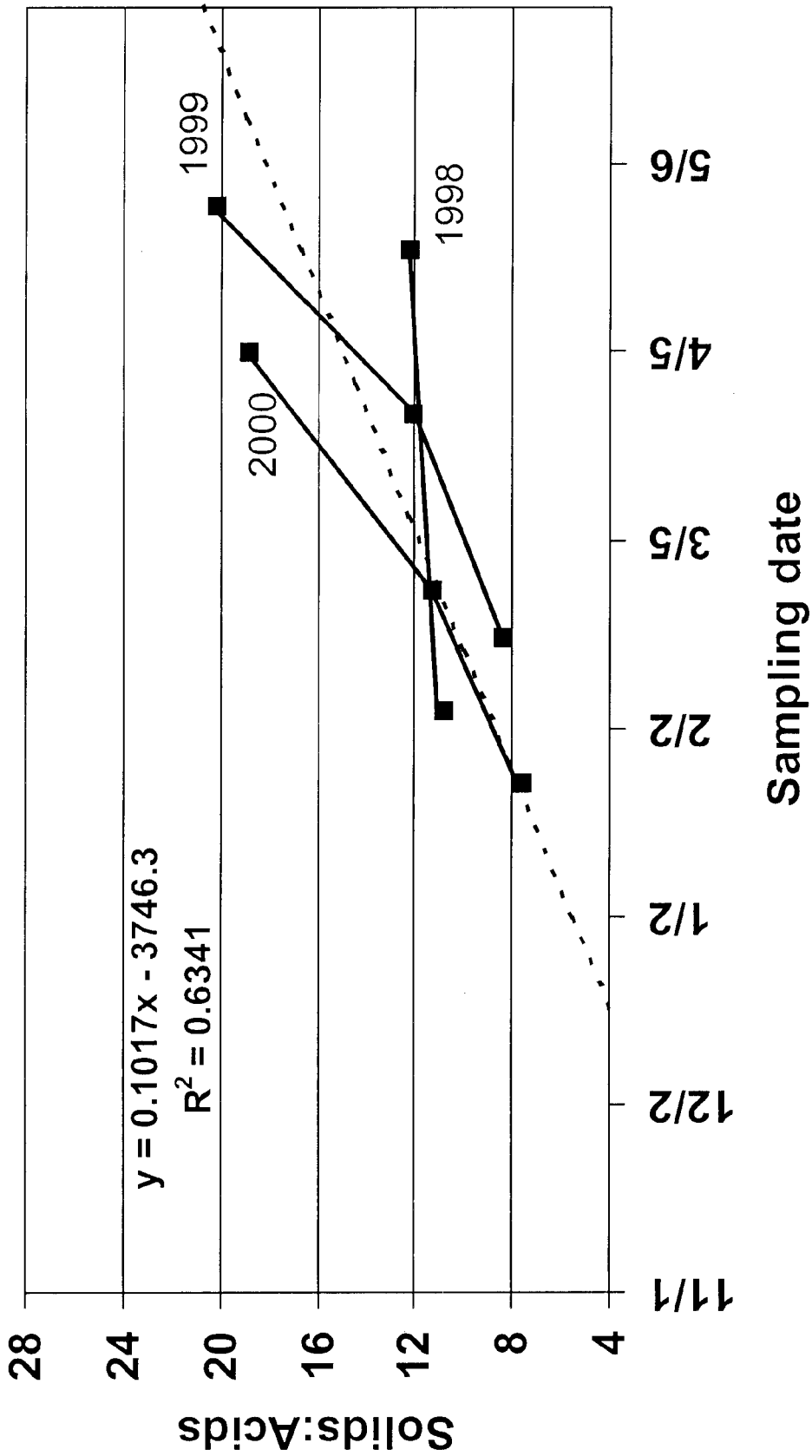
Figure 4A. Solids:Acid of TDE3 at Santa Paula, CA

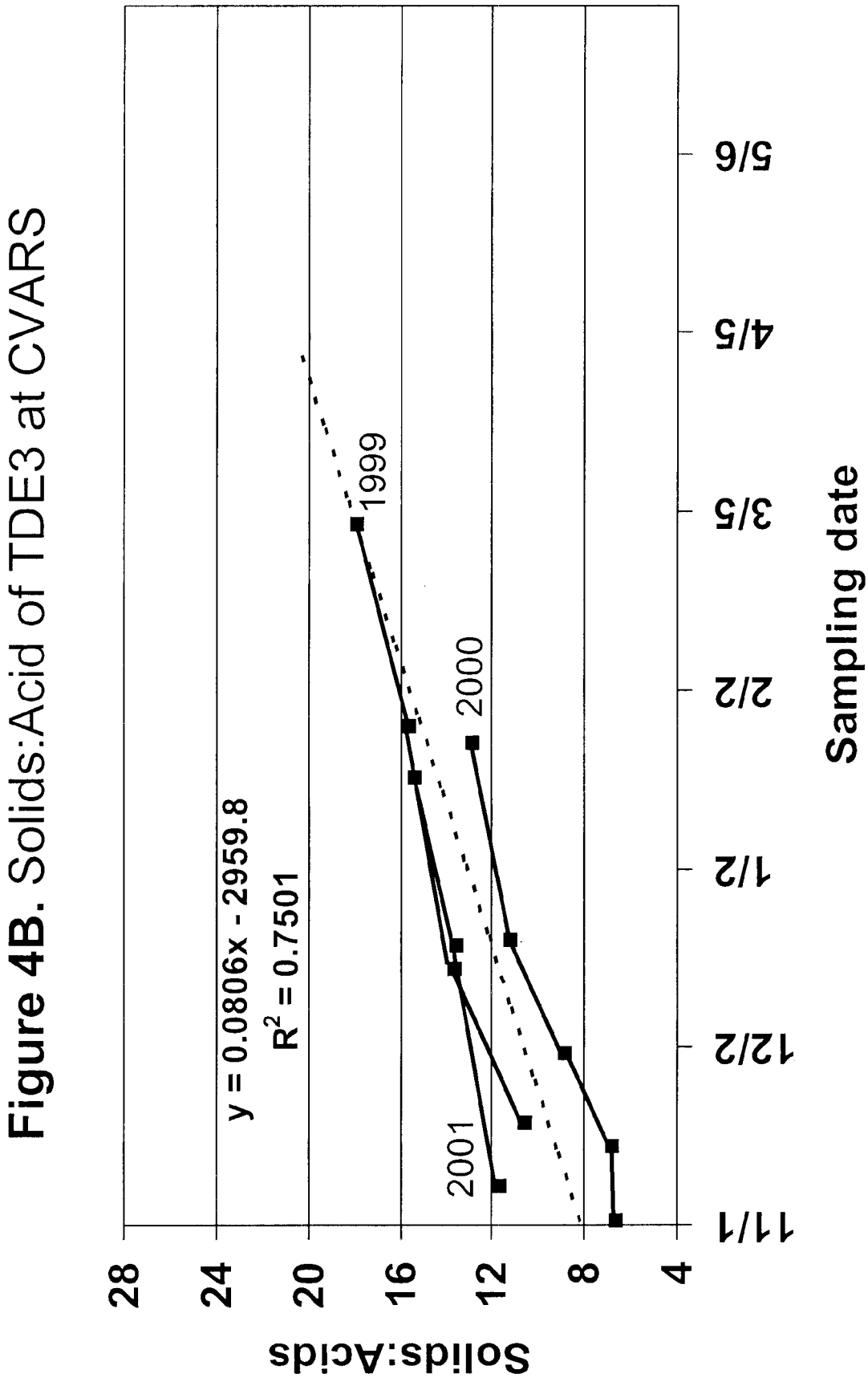
Figure 4B. Solids:Acid of TDE3 at CVARS
y = 0.0806x - 2959.8
R2 = 0.7501
1999
2000
2001
Solids:Acids
28
24
20
16
12
8
4
11/1
12/2
1/2
2/2
3/5
4/5
5/6
Sampling date

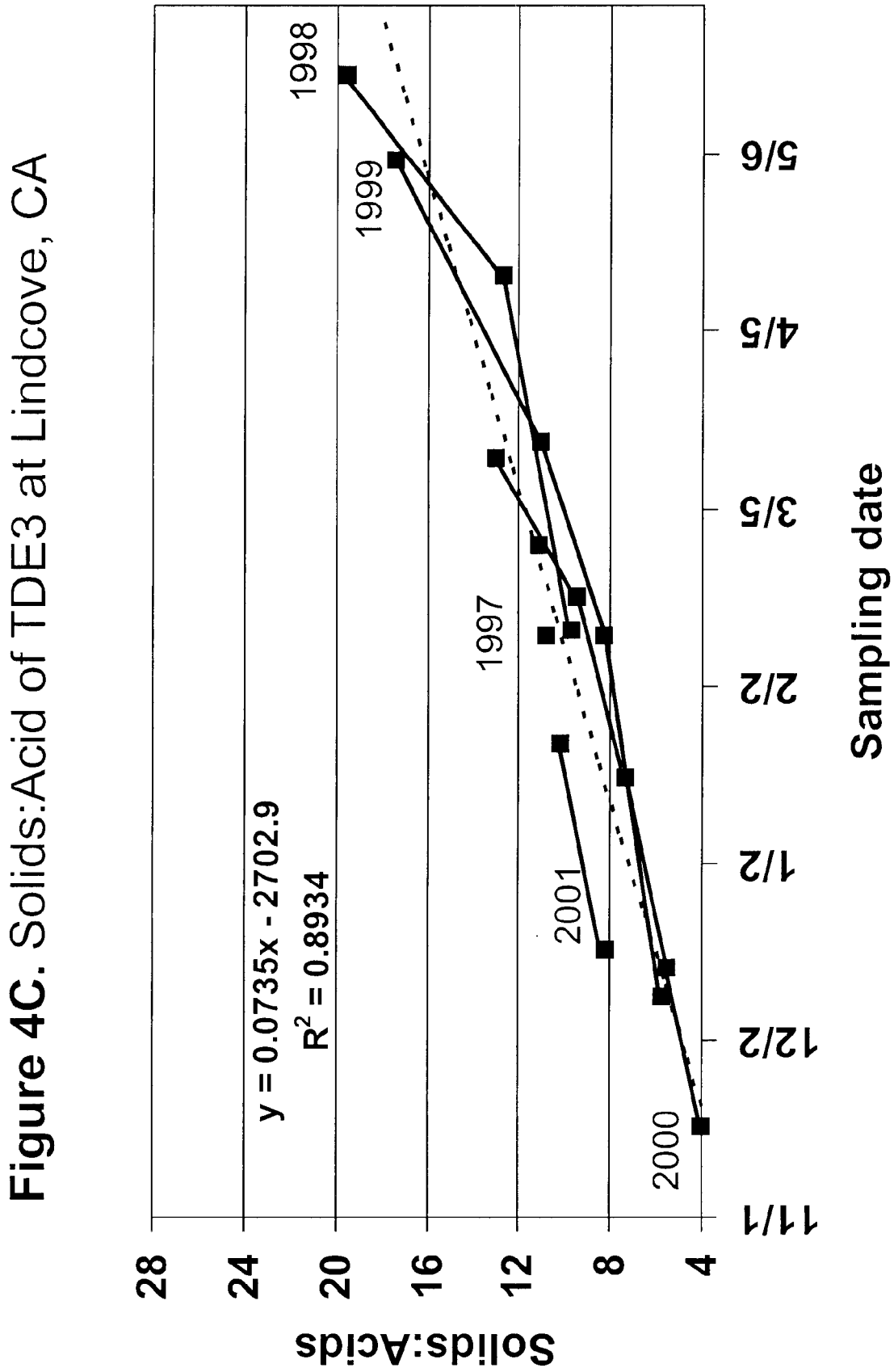
Figure 4C. Solids:Acid of TDE3 at Lindcove, CA
y = 0.0735x - 2702.9
R2 = 0.8934
1998
1999
1997
2001
2000
28
24
20
16
12
8
4
Solids:Acids
11/1
12/2
1/2
2/2
3/5
4/5
5/6
Sampling date

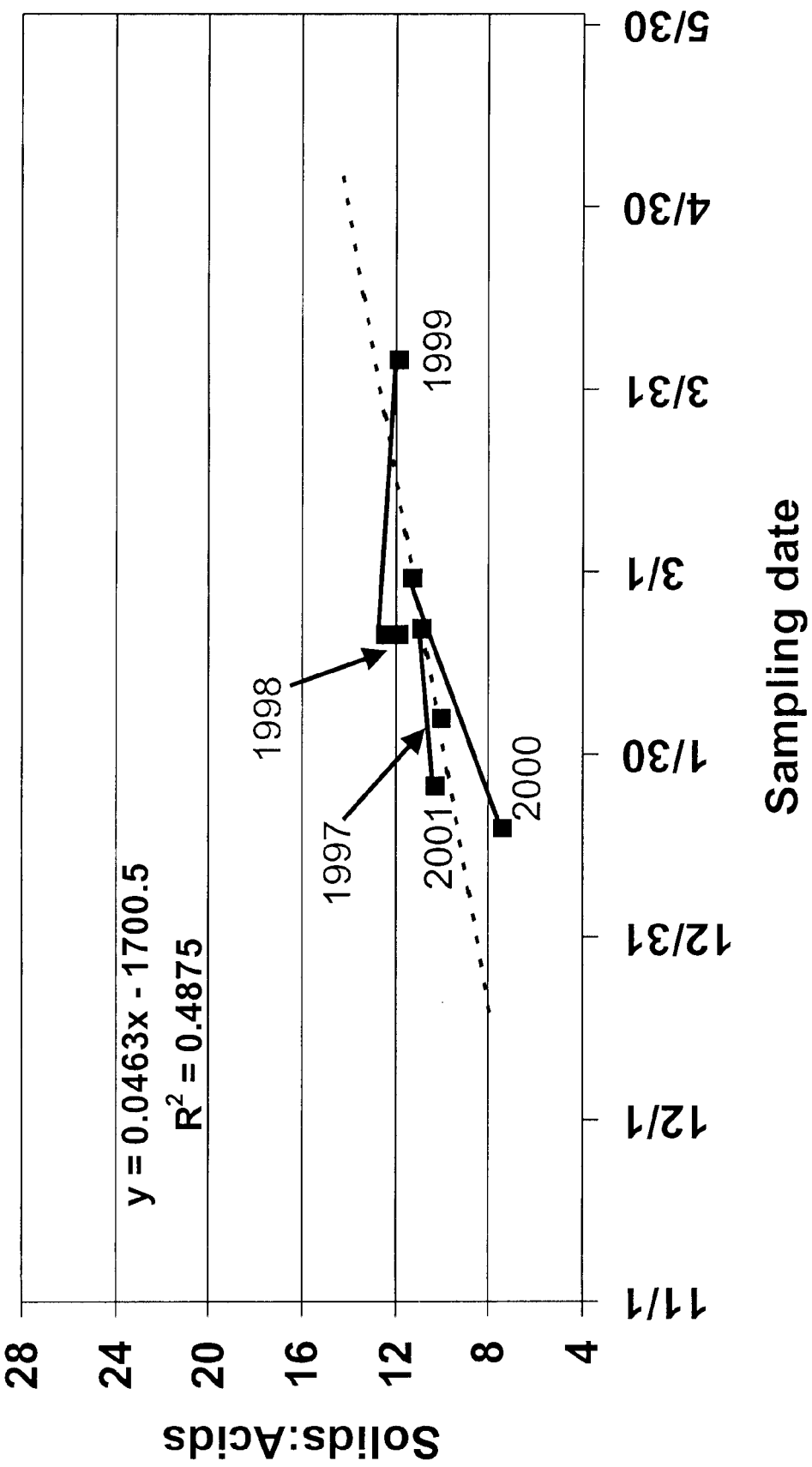
Figure 4D. Solids:Acid of TDE3 at Valley Center, CA

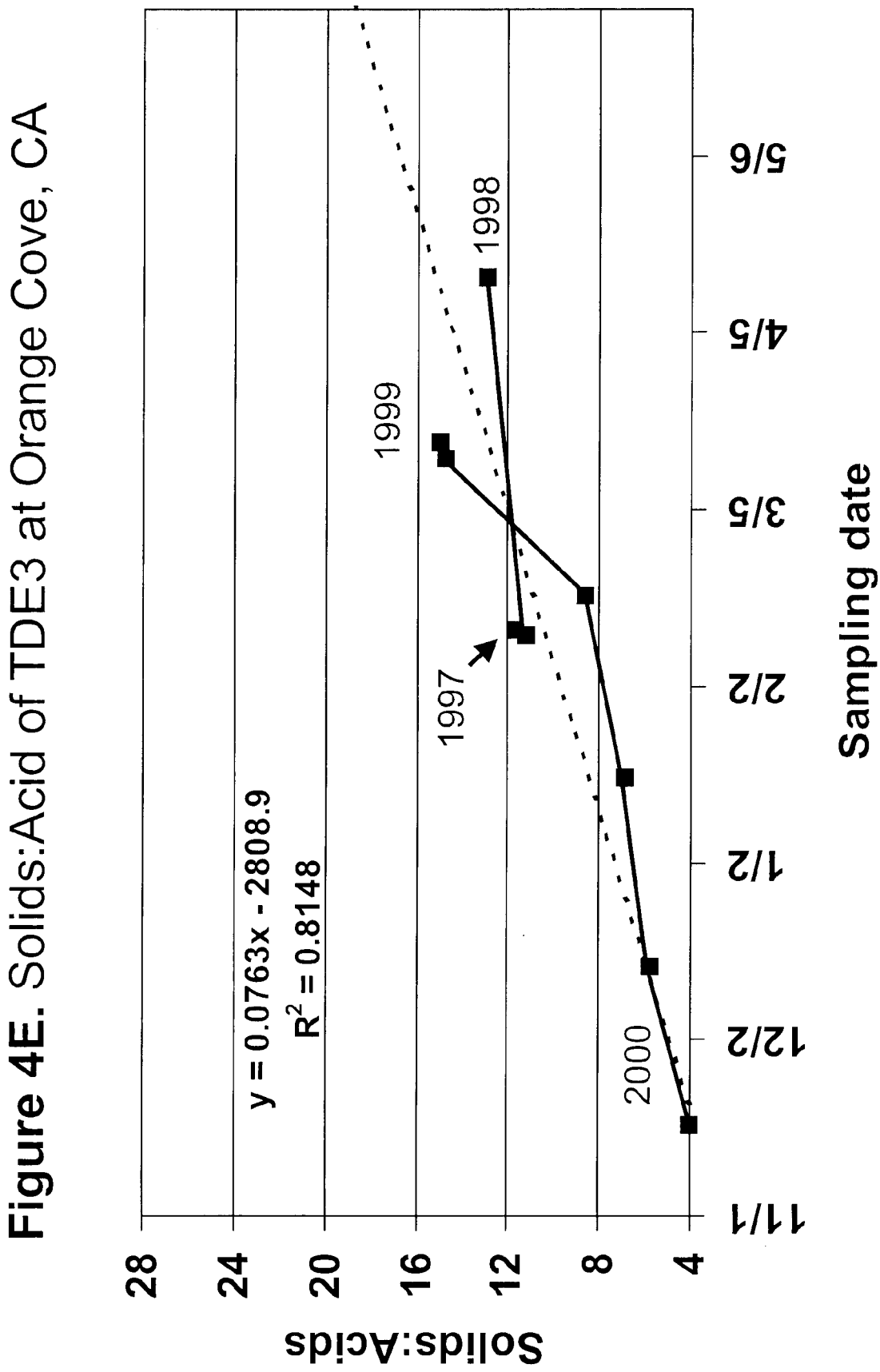
Figure 4E. Solids:Acid of TDE3 at Orange Cove, CA

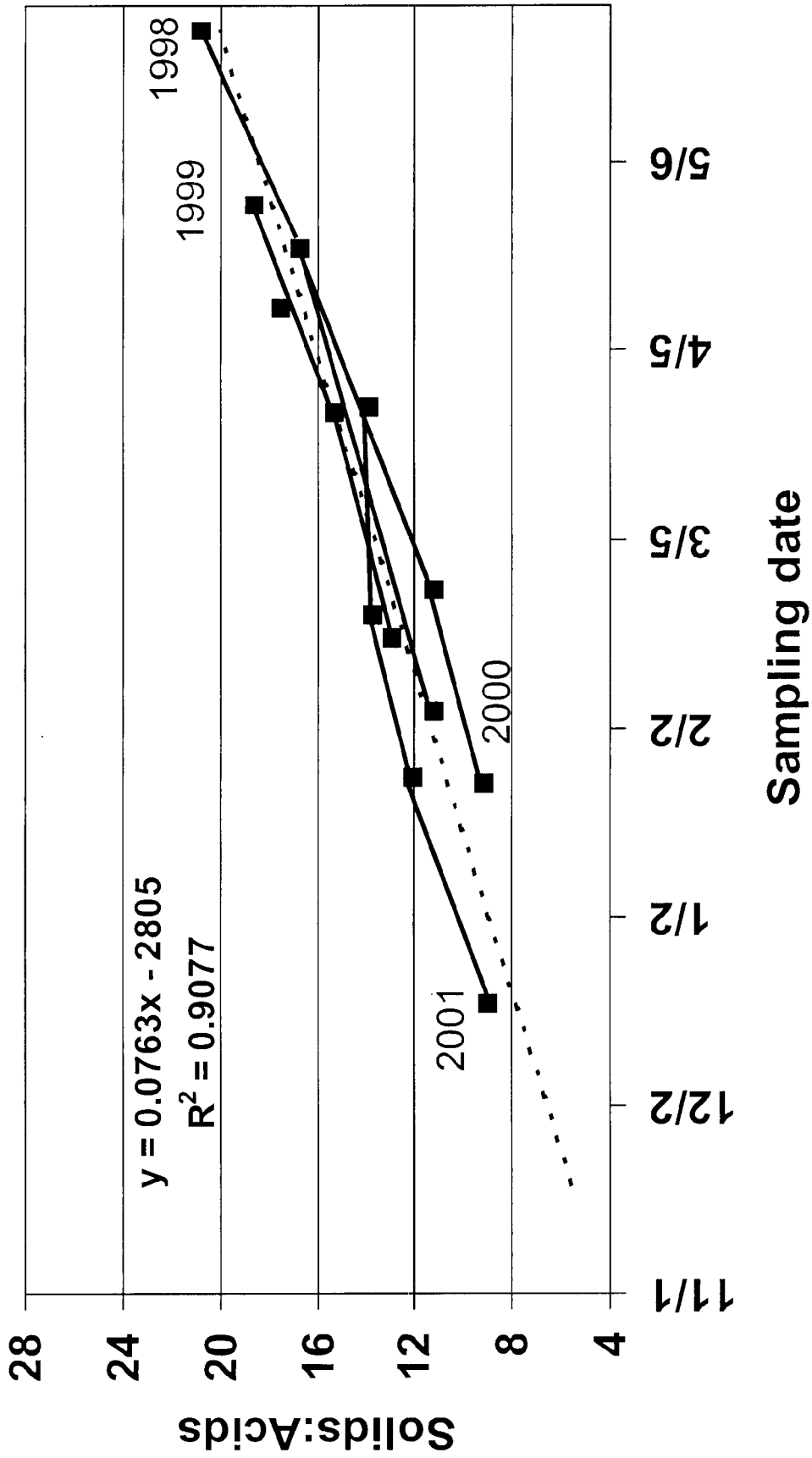
Figure 4F. Solids:Acid of TDE3 at Ojai, CA

UNITED STATES PATENT AND TRADEMARK OFFICE

CERTIFICATE OF CORRECTION

PATENT NO. : PP 15,703 P3
DATED : March 29, 2005
INVENTOR(S) : Mikeal L. Roose et al.

It is certified that error appears in the above-identified patent and that said Letters Patent is hereby corrected as shown below:

Title page,
Item [75], Inventors, change the second inventor's name from "Timothy A. Williams" to read -- Timothy E. Williams --.

Signed and Sealed this

Thirteenth Day of September, 2005

JON W. DUDAS
*Director of the United States Patent and Trademark Office*